US009817119B2

United States Patent
Kobayashi et al.

(10) Patent No.: US 9,817,119 B2
(45) Date of Patent: Nov. 14, 2017

(54) ULTRASOUND IMAGE PROCESSING APPARATUS AND PROGRAM

(75) Inventors: Yoshiyuki Kobayashi, Mitaka (JP); Satoshi Tanaka, Mitaka (JP); Futoshi Ogata, Mitaka (JP); Masaru Murashita, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 408 days.

(21) Appl. No.: 14/116,243

(22) PCT Filed: Apr. 2, 2012

(86) PCT No.: PCT/JP2012/058800
§ 371 (c)(1),
(2), (4) Date: Nov. 7, 2013

(87) PCT Pub. No.: WO2012/160873
PCT Pub. Date: Nov. 29, 2012

(65) Prior Publication Data
US 2014/0086014 A1    Mar. 27, 2014

(30) Foreign Application Priority Data

May 25, 2011 (JP) ................................. 2011-117028

(51) Int. Cl.
G01S 15/89 (2006.01)
G01S 7/52 (2006.01)
A61B 8/08 (2006.01)

(52) U.S. Cl.
CPC ...... G01S 15/8981 (2013.01); G01S 7/52066 (2013.01); G01S 7/52077 (2013.01);
(Continued)

(58) Field of Classification Search
CPC ............. G01S 15/8981; G01S 7/52066; G01S 7/52077; A61B 8/5207; A61B 8/5269
(Continued)

(56) References Cited

U.S. PATENT DOCUMENTS 6,050,948 A * 4/2000 Sasaki .................. A61B 8/488
  600/453
2002/0094114 A1* 7/2002 Ogino ...................... G06T 5/20
  382/128
(Continued)

FOREIGN PATENT DOCUMENTS

JP   02-164352 A   6/1990
JP   03-55048 A    3/1991
(Continued)

OTHER PUBLICATIONS

English Machine Translation of JP 2005318921.*
(Continued)

*Primary Examiner* — James R Hulka
*Assistant Examiner* — John T Nolan
(74) *Attorney, Agent, or Firm* — Westerman, Hattori, Daniels & Adrian, LLP

(57) ABSTRACT

An ultrasound diagnostic apparatus generates Doppler waveform images whose visibility is improved appropriately in accordance with changes in measurement conditions. The ultrasound diagnostic apparatus includes a frequency-analyzing unit that generates frequency spectrum data on Doppler shift frequency components of ultrasonic waves that are received after being transmitted towards a subject and reflected in the subject, and a line data generating unit for generating line data, wherein arrays of multiple pixels are stipulated according to the corresponding frequencies and each pixel value represents the magnitude of the Doppler shift frequency component, based on the frequency spectrum data. The ultrasound diagnostic apparatus determines whether or not each pixel of line data at a previously appointed time point is a noise pixel, and the values of pixels that are determined to be noise pixels are adjusted by (Continued)

multiplying the pixel value with a weighting factor (w) of 0 to less than 1.

5 Claims, 10 Drawing Sheets

(52) U.S. Cl.
CPC ............ *A61B 8/488* (2013.01); *A61B 8/5207* (2013.01); *A61B 8/5269* (2013.01)

(58) Field of Classification Search
USPC .......................................................... 367/90
See application file for complete search history.

(56) References Cited

U.S. PATENT DOCUMENTS

| 2003/0158484 | A1* | 8/2003 | Pan ..................... G01S 15/8981 600/453 |
|---|---|---|---|
| 2007/0016073 | A1* | 1/2007 | Kim ......................... A61B 8/06 600/473 |
| 2009/0069683 | A1* | 3/2009 | Miyasaka ............ A61B 5/6843 600/443 |
| 2009/0163816 | A1 | 6/2009 | Azuma et al. |
| 2010/0168574 | A1* | 7/2010 | Takabayashi ............ A61B 8/08 600/443 |
| 2011/0063945 | A1* | 3/2011 | Kim ......................... A61B 8/06 367/7 |

FOREIGN PATENT DOCUMENTS

| JP | 04-12741 A | 1/1992 |
|---|---|---|
| JP | 04-122359 A | 4/1992 |
| JP | 07-241291 A | 9/1995 |
| JP | 11-33024 A | 2/1999 |
| JP | 2002-183709 A | 6/2002 |
| JP | 2003-245279 A | 9/2003 |
| JP | 2005-318921 A | 11/2005 |
| JP | 2006-326291 A | 12/2006 |
| JP | 2009-291325 A | 12/2009 |
| WO | 2005/115248 A1 | 12/2005 |

OTHER PUBLICATIONS

Office Action dated Nov. 5, 2014, issued in corresponding Chinese Patent Application No. 201280025334.3, with English Translation (14 pages).
English Translation of the International Preliminary Report on Patentability of PCT/JP2012/058800, dated Dec. 5, 2013 with forms PCT/IB/326, PCT/IB/373, PCT/IB/338 and PCT/ISA/237 (13 pages).
Notice of Grounds for Rejection for JP 2011-117028, dated Jul. 10, 2012.
Notice of Grounds for Rejection for JP 2011-117028, dated Sep. 18, 2012.
Notice of Grounds for Rejection for JP2011-117028, dated Apr. 2, 2013.
International Search Report for PCT/JP2012/058800, dated May 15, 2012.

* cited by examiner

TIME ADDRESS At

VELOCITY ADDRESS Av

FIG. 2

# ULTRASOUND IMAGE PROCESSING APPARATUS AND PROGRAM

TECHNICAL FIELD

The present invention relates to an ultrasound image processing apparatus, and particularly to an improvement for the processing performed for noise pixels.

BACKGROUND ART

Ultrasound diagnostic apparatuses that measure, for example, the blood flow velocity of a subject by using the Doppler method are widely employed. Such ultrasound diagnostic apparatuses are, for example, continuous wave Doppler devices, pulse-Doppler devices, etc. The continuous wave Doppler device transmits an ultrasonic wave as a continuous wave to a subject. Thereafter, the device sequentially receives the ultrasonic waves reflected from the subject along the time axis, and employs the Doppler shift frequency components of the ultrasonic waves to display the Doppler waveforms that represent a temporal change. The pulse-Doppler device transmits a pulse-modulated ultrasonic wave to a subject at a predetermined time interval. Thereafter, the device receives, at the timing consonant with the depth of the region to be examined, the ultrasonic waves reflected from the subject, and employs the Doppler shift frequency components of the ultrasonic waves to display the Doppler waveforms.

For the pulse-Doppler device, the velocity to be measured is limited in accordance with the time interval of transmission of the pulse modulated wave. On the other hand, there is no such limitation for the continuous wave Doppler device, and the upper limit of the velocity to be measured is higher than that for the other devices that employ the Doppler method. Therefore, the continuous wave Doppler device is frequently employed to rapidly diagnose the presence/absence of blood flow due to a circulatory system disease.

Generally, noise may appear on the image obtained by the ultrasound diagnostic apparatus due to external noise, thermal noise, non-linearity of the circuitry, etc., and may degrade the visibility of the image. Therefore, a technique for improving the visibility of the image obtained by the ultrasound diagnostic apparatus has been proposed. For example, in patent documents 1 to 3, a technique is described for enhancing the contour of an image obtained by the ultrasound diagnostic apparatus. The ultrasound diagnostic apparatus described in these patent documents calculates the mean value and the variance of pixel values for a group of pixels in a predetermined area that includes a target pixel. Thereafter, the pixel value of the target pixel is changed based on differences between the value of the target pixel and the mean and the variance thus obtained, and the visibility of the image is increased.

Further, an ultrasonic Doppler diagnostic apparatus is described in patent document 4. This apparatus obtains, as a data sample area, an area of a Doppler waveform image located at a predetermined distance from the base line that indicates a velocity of zero, and employs the luminance distribution for the individual pixels in this area to detect a reference noise level. Thereafter, the reference noise level is employed to perform automatic tracing for the Doppler waveform.

CITATION LIST

Patent Documents

PTL 1: Japanese Patent Laid-Open No. Hei 2-164352
PTL 2: Japanese Patent Laid-Open No. Hei 4-122359
PTL 3: Japanese Patent Laid-Open No. Hei 4-12741
PTL 4: Japanese Patent Laid-Open No. Hei 7-241291

SUMMARY OF INVENTION

Technical Problem

The continuous wave Doppler device employs a received ultrasonic signal to obtain a frequency spectrum for a Doppler shift frequency component. Then, based on a plurality of frequency spectrums sequentially obtained as time elapses, a Doppler waveform image shown in FIG. 10 is displayed. In this drawing, the horizontal axis represents time, and the vertical axis represents a velocity. In the Doppler waveform image, each of the pixel values of a plurality of pixels, arranged on a line along the velocity axis, represents the frequency spectrum at the corresponding time. In this manner, the continuous wave Doppler device displays a Doppler waveform image based on a plurality of frequency spectrums sequentially obtained as time elapses.

The continuous wave Doppler device may change, while performing diagnosis, the measurement conditions, such as the position of a subject, the location for transmission and reception of an ultrasonic wave, and the ultrasonic wave transmission and reception directions. In this case, it is preferable that the processing for appropriately improving the visibility in accordance with the change of the measurement conditions be performed for frequency spectrum data that are obtained sequentially as time elapses. However, according to the prior art, it is sometimes difficult to perform the processing in consonance with the change of the measurement conditions.

The present invention is provided by resolving this problem. One objective of the present invention is to generate a Doppler waveform image, for which visibility is appropriately increased in accordance with a change of measurement conditions.

Solution to Problem

According to the present invention, an ultrasound image processing apparatus, which generates a Doppler waveform image that represents a velocity of a subject to be measured, is characterized by comprising:

a frequency-analyzing unit, for generating frequency spectrum data on Doppler shift frequency components of ultrasonic waves that have been transmitted toward a subject and reflected from the subject, and are thereafter received;

a line data generating unit, for employing the frequency spectrum data to generate line data, for which arrangement of a plurality of pixels is stipulated in accordance with a corresponding frequency, and individual pixel values represent magnitudes of the Doppler shift frequency components;

a window designating unit for designating a computation window region in a Doppler waveform image that would be formed by employing a plurality sets of line data generated in a time series;

a trend value calculating unit for calculating a trend value that indicates a tendency for magnitudes of pixel values in the window region;

a threshold value determining unit for employing a plurality of pixel values in a predetermined area of the Doppler waveform image to determine a threshold value for evaluation of the trend value; and a pixel value adjusting unit for adjusting a pixel value of a target pixel in the window region based on a result obtained by comparing the trend value with the evaluation threshold value, and for outputting the adjusted pixel value as a new pixel value for the target pixel.

There is a tendency for the Doppler waveform image whereby the pixel value of a pixel in the area near the noise pixel is lower than a predetermined value. In the present invention, based on this principle, comparison between the trend value with the evaluation threshold value is performed in the window region corresponding to the target pixel, and the pixel value is adjusted for the target pixel, for which the possibility of a noise pixel is high. As a result, the visibility of the Doppler waveform image can be increased. The trend value of this invention represents the tendency of the magnitude of the pixel value in the window region. A trend value employed is, for example, a statistical value, such as the mean value, the median or a central value, or a value obtained by adding a constant value to the mean value.

Further, the ultrasound image processing apparatus according to the present invention preferably includes:

a dispersion calculating unit for obtaining dispersion of pixel values included in the window region, wherein the pixel value adjusting unit not only compares the trend value with the evaluation threshed value, but also compares the dispersion with a predetermined second evaluation threshold value, and employs the obtained results to adjust the pixel value of the target pixel in the window region and outputs the adjusted pixel value as a new pixel value for the target pixel.

There is a tendency for the Doppler waveform image whereby the pixel value of a pixel in the area near the noise pixel is lower than a predetermined value. Moreover, there is a tendency that dispersion of the pixel values of a plurality of pixels in the area near the noise pixel is reduced. In the present invention, based on this principle, not only the results obtained by comparing the trend value with the evaluation threshold value in the window region corresponding to the target pixel, but also the dispersion of the pixel values included in the window region is employed to adjust the pixel value for the target pixel, for which the possibility of a noise pixel is high. As a result, the visibility of the Doppler waveform image can be increased.

Furthermore, it is preferable for the ultrasound image processing apparatus of this invention that the predetermined area of the Doppler waveform image be an area located apart from the base line indicating a velocity of zero, in a direction along the pixel arrangement of the line data, at a distance equivalent to a predetermined number of pixels, and that, for each of the plurality of sets of line data that form the Doppler waveform image, the threshold value determining unit calculate statistical values with respect to the plurality of pixel values in an area that is one part of the predetermined area, and calculate the evaluation threshold value based on the statistical values obtained for the individual sets of line data.

According to the present invention, the threshold value for evaluation of the trend value is determined based on the plurality of pixel values in the predetermined area of the Doppler waveform image. Preferably, the predetermined area is provided by taking into account the tendency of the pixel value of the noise pixel in the Doppler waveform image. According to the present invention, the predetermined area is designated at a location apart at a distance equivalent to a predetermined number of pixels in the direction along the pixel arrangement of the line data. As a result, the predetermined area is set in an area where noise tends to be increased, and the tendency of the pixel value of the noise pixel can be appropriately provided for the evaluation threshold value.

Further, it is preferable for the ultrasound image processing apparatus of this invention that the frequency-analyzing unit include:

a measurement range acquiring unit for obtaining a velocity measurement range in accordance with an operation by a user;

a sampling unit for performing sampling for a signal received based on the received ultrasonic wave by employing a sampling frequency higher than a bandwidth that corresponds to the velocity measurement range and that is extended between positive and negative Doppler shift frequencies; and a converting unit for generating the frequency spectrum data based on a Fourier transform for the received signal obtained by sampling.

According to the present invention, sampling for a received signal is performed by employing a sampling frequency higher than a bandwidth that corresponds to the velocity measurement range and is extended between the positive and negative Doppler shift frequencies. As a result, the frequency for the generation of an inappropriate image due to aliasing can be reduced. It should be noted that the negative Doppler shift frequency is a frequency having a Doppler shift frequency component, for which phase rotation is in the direction opposite that of the positive Doppler shift frequency.

Moreover, according to the present invention, an ultrasound image processing program, which permits a processor to perform a process for generating a Doppler waveform image that represents a velocity of a subject to be measured, is characterized by permitting the processor to perform:

a frequency-analyzing process, for generating frequency spectrum data on Doppler shift frequency components of ultrasonic waves that have been transmitted toward a subject and reflected from the subject, and are thereafter received;

a line data generating process, for employing the frequency spectrum data to generate line data, for which arrangement of a plurality of pixels is stipulated in accordance with a corresponding frequency, and individual pixel values represent magnitudes of the Doppler shift frequency components;

a window designating process, for designating a computation window region in a Doppler waveform image that would be formed by employing a plurality sets of line data generated in a time series;

a trend value calculating process, for calculating a trend value that indicates a tendency for magnitudes of pixel values in the window region;

a threshold value determining process, for employing a plurality of pixel values in a predetermined area of the Doppler waveform image to determine a threshold value for evaluation of the trend value; and a pixel value adjusting process, for adjusting a pixel value of a target pixel in the window region based on a result obtained by comparing the trend value with the evaluation threshold value.

Advantageous Effects of Invention

According to the present invention, a Doppler waveform image can be generated with the visibility being appropriately increased in accordance with the change of the measurement conditions.

BRIEF DESCRIPTION OF DRAWINGS

FIG. 2 A conceptual diagram showing the arrangement of pixel values stored in a buffer memory.

DESCRIPTION OF EMBODIMENT (1) Configuration of Ultrasound Diagnostic Apparatus

Figure 1:
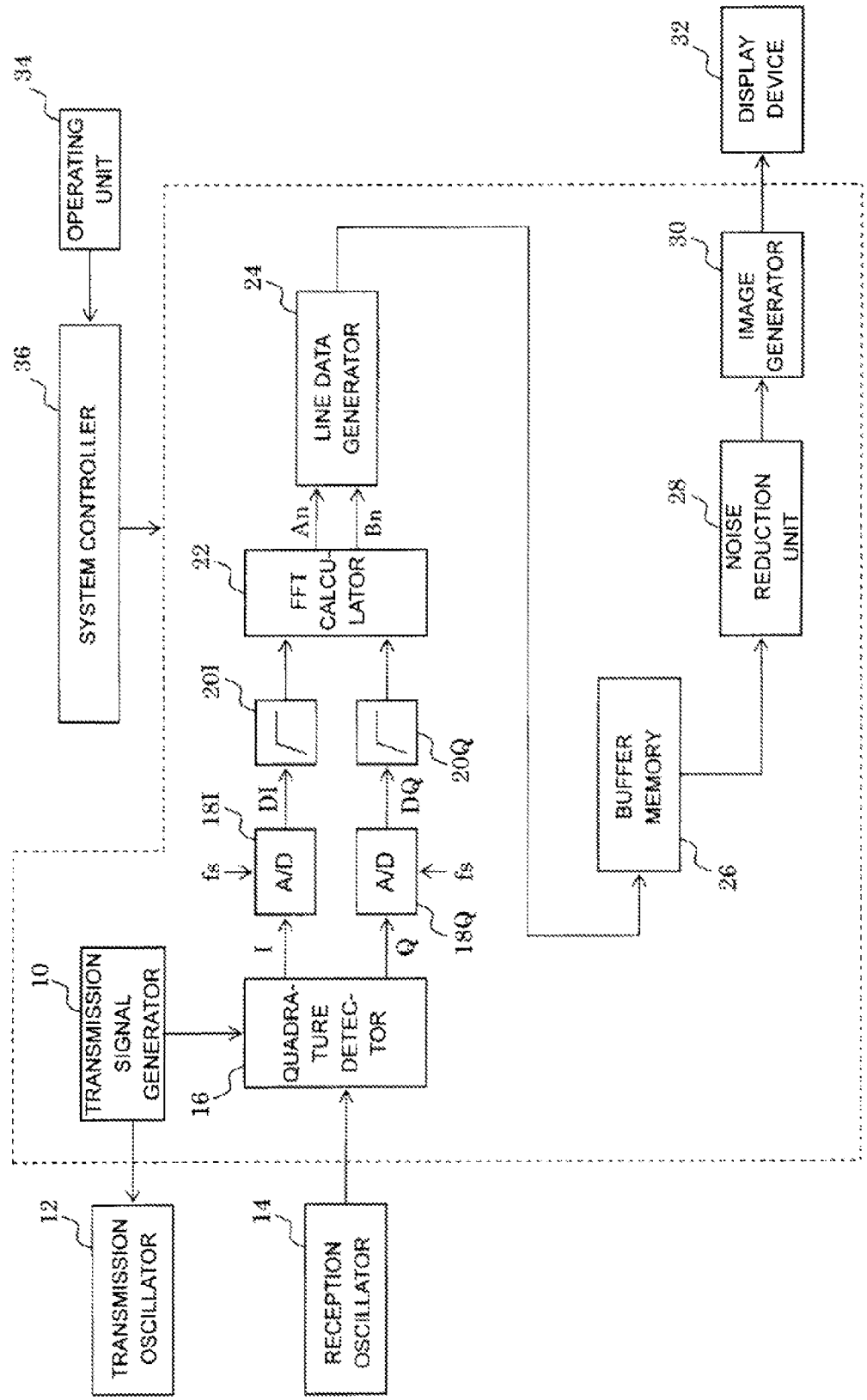
FIG. 1 A diagram illustrating the configuration of an ultrasound diagnostic apparatus according to one embodiment of the present invention.

The configuration of an ultrasound diagnostic apparatus according to one embodiment of the present invention is shown in FIG. 1. The ultrasound diagnostic apparatus transmits an ultrasonic wave as a continuous wave to a subject, receives the ultrasonic wave that is reflected from the subject, and displays a Doppler waveform image on a display device 32 based on the received ultrasonic wave. That is, this ultrasound diagnostic apparatus is a continuous wave Doppler apparatus employed for diagnosis of blood flows, for example. The individual components of the ultrasound diagnostic apparatus are controlled by a system controller 36 in accordance with an instruction entered by a user on an operating unit 34.

The configuration of the ultrasound diagnostic apparatus will be described. A transmission signal generator 10 generates, as a transmission signal, an electrical signal having a continuous waveform, and outputs the transmission signal to a transmission oscillator 12. The transmission oscillator 12 is provided by employing, for example, a piezoelectric element that is vibrated in accordance with an alternating voltage that is applied. Upon receiving the transmission signal output by the transmission signal generator 10, the transmission oscillator 12 transmits an ultrasonic wave as a continuous wave to the subject.

After the ultrasonic wave has been transmitted by the transmission oscillator 12 and reflected in the subject, the reflected wave is received by a reception oscillator 14. As with the transmission oscillator 12, the reception oscillator 14 is provided by employing, for example, a piezoelectric element. The reception vibrator 14 converts the received ultrasonic wave into an electrical signal, and outputs the signal as a reception signal to a quadrature detector 16.

The transmission signal generator 10 not only outputs a transmission signal to the transmission oscillator 12, but also outputs a local signal for quadrature detection to the quadrature detector 16. The local signal may be a signal having the same frequency as the transmission signal. For the configuration in this case, the transmission signal generator 10 may output the transmission signal unchanged as a local signal.

The quadrature detector 16, A/D converters 18I and 18Q, high-pass filters 20I and 20Q, and an FFT calculator 22 serve as a frequency-analyzing unit that generates a frequency spectrum data for the Doppler shift frequency component of a received ultrasonic wave.

The quadrature detector 16 employs a local signal to extract from the received signal an in-phase signal I and a quadrature-phase signal Q. The quadrature detector 16 thereafter performs low-pass filtering for the extracted in-phase signal I and the quadrature-phase signal Q to reduce harmonic components, and outputs the resultant signals to the A/D converters 18I and 18Q, respectively.

The in-phase signal I and the quadrature-phase signal Q are those obtained by extracting, from the received signal, the Doppler shift frequency components with a phase difference of 90°, and the frequencies of the signals match the Doppler shift frequency.

The A/D converters 18I and 18Q perform sampling for the in-phase signal I and the quadrature-phase signal Q based on a predesignated sampling frequency fs, and convert into digital signals the in-phase signal I and the quadrature-phase signal Q, for which sampling has been performed. Thereafter, an in-phase signal DI and a quadrature-phase signal DQ that are obtained as digital signals are output to the high-pass filters 20I and 20Q.

The high-pass filters 20I and 20Q perform high-pass filtering for the in-phase signal DI and the quadrature-phase signal DQ to reduce low-frequency noise, such as clutter, included in the in-phase signal DI and the quadrature-phase signal DQ. The clutter is noise caused by ultrasonic waves reflected from biological tissues, and the level of the clutter is very much higher than the level of the ultrasonic wave reflected from, for example, blood. When the high-pass filters 20I and 20Q are provided, a dynamic range required for the succeeding signal processing can be reduced, and measurement accuracy can be improved.

The high-pass filters 20I and 20Q output, to the FFT calculator 22, the in-phase signal DI and the quadrature-phase signal DQ obtained through the high-pass filtering. The FFT calculator 22 performs a fast Fourier transform for the in-phase signal DI and the quadrature-phase signal DQ, and outputs, to a line data generator 24, a frequency spectrum signal obtained by the fast Fourier transform. The frequency spectrum signal is represented by complex discrete value $An+jBn$ (n is an integer) where a complex number is correlated as a frequency spectrum value with each discrete frequency value.

The line data generator 24 employs the frequency spectrum signal for one period in the frequency region, and generates, as line data, a group of pixels arranged on a line along the velocity axis in the Doppler waveform image. Specifically, the line data generator 24 calculates the absolute values of the individual complex discrete values included in the frequency spectrum signal, and employs the individual absolute values to calculate sequential data that represent the frequency spectrum. For calculation of this data, the process, such as the logarithmic amplification for adjusting the level, may be performed together with the logarithmic conversion for the absolute values.

The line data generator 24 employs the thus-obtained frequency spectrum data to provide pixel values for the individual pixels of the group arranged on a line along the velocity axis. Thereafter, a set of pixel values for one line is output as one set of line data to a buffer memory 26. The line data thus generated is a set of pixel values, according to which the arrangement of a plurality of pixels is defined based on with the Doppler shift frequency consonant with the individual pixels, and the individual pixel values represent the magnitudes of the Doppler shift frequency components.

Figure 2:
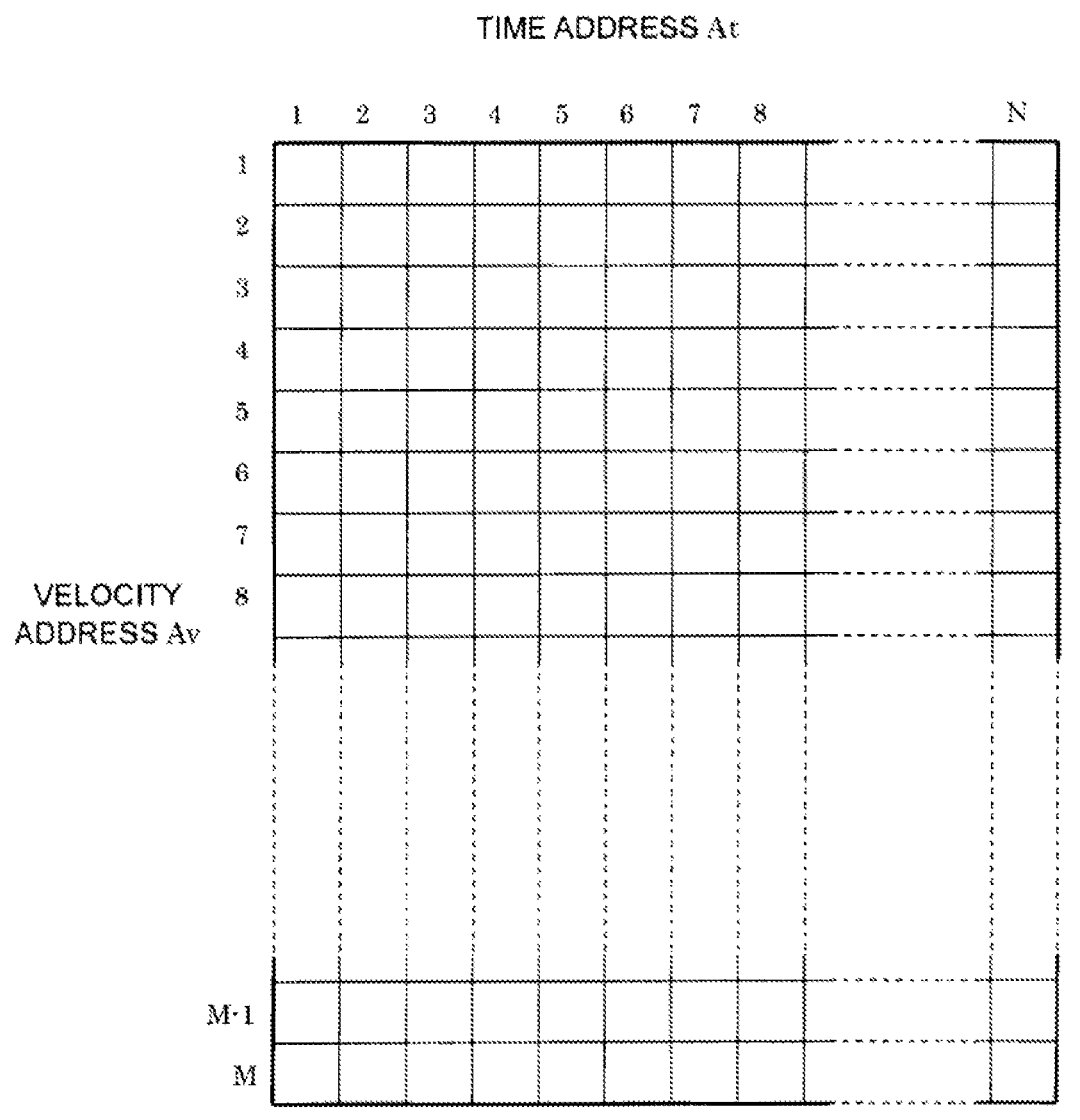

Based on frequency spectrum signals sequentially output by the FFT calculator 22 as time elapses, the line data generator 24 generates line data, and outputs the line data to the buffer memory 26. The concept of the arrangement of pixel values stored in the buffer memory 26 is illustrated in FIG. 2. In this drawing, the horizontal direction corresponds to the direction along the time axis, and the vertical direction corresponds to the direction along the velocity axis. The concept of the arrangement of pixel values is illustrated in FIG. 2, and the arrangement where pixels having luminance levels that correspond to the pixel values are provided at the locations of the individual pixel values is a Doppler waveform image. Therefore, in the following description, the area shown in FIG. 2 where the pixel values are conceptually arranged is called a pixel arrangement area.

At the individual positions in the pixel arrangement area, velocity addresses Av, 1 to M, are allocated along the velocity axis, and time addresses At, 1 to N, are allocated along the time axis. M pixel values arranged on a line along the velocity axis are provided as one set of line data. The rightmost line data are the oldest data stored, and the leftmost line data are the latest data stored.

Each time one set of line data is output by the line data generator 24, the rightmost line data in the buffer memory 26 is erased, and N−1 sets of line data located on the left of the rightmost line data are shifted to the right by a distance equivalent to one pixel. Then, new line data are stored at the leftmost velocity address.

Referring again to FIG. 1, each time new line data are stored in the buffer memory 26, a noise reduction unit 28 performs a noise reduction process for one set of line data at the predesignated time address, and outputs the resultant line data to an image generator 30. The image generator 30 generates Doppler waveform image data based on the line data that are sequentially output by the noise reduction unit 28 as time elapses, and displays the Doppler waveform image on the display device 32.

For the ultrasound diagnostic apparatus of this embodiment, the components that perform the digital processing; i.e., the high-pass filters 20I and 20Q, the FFT calculator 22, the line data generator 24, the noise reduction unit 28, and the image generator 30, may be provided by employing a processor. The processor reads a program stored in the memory included in the ultrasound diagnostic apparatus, and performs the digital signal processing for the individual components. This processor is incorporated in a general-purpose computer, such as a personal computer, which may be included in the ultrasound diagnostic apparatus.

(2) Noise Reduction Process

Next, the noise reduction process will be described. In the noise reduction process, the individual pixels indicated by one set of line data at a predesignated time address are examined to determine whether or not these pixels are noise pixels. For a pixel that is regarded as a noise pixel as a result of determination, the value of the pertinent pixel is multiplied by a weighting factor w that ranges from 0 to smaller than 1 to adjust the pixel value.

Each time new line data are output by the line data generator 24, the line data stored in the buffer memory 26 are shifted. Therefore, each time new line data are output by the line data generator 24, line data at the predesignated time address are updated, and the line data to be processed are updated.

Figure 3:
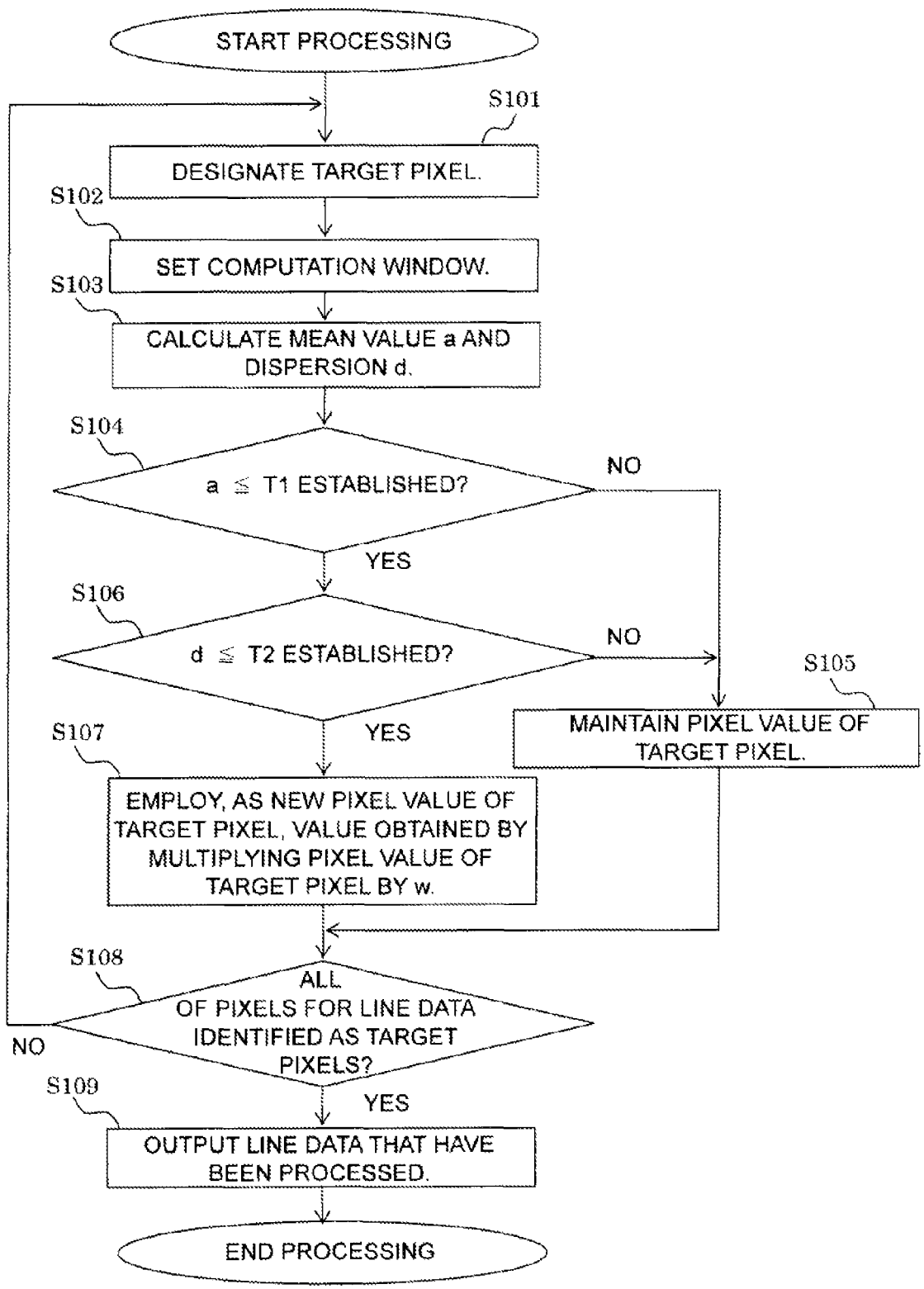
FIG. 3 A flowchart for a noise reduction process.

FIG. 3 is a flowchart showing the noise reduction process. The noise reduction unit 28 designates, as a target pixel, one of a plurality of pixels indicated by line data at a predesignated time address (S101). Then, a computation window is set that includes the target pixel, and that has a length equivalent to P pixels along the velocity axis (in the vertical direction), and has a length equivalent to Q pixels along the time axis (in the horizontal direction) (S102). Here, P and Q are integers equal to or greater than 2. The integers P and Q may be defined as constant values, or may be acquired based on an operation performed by a user. That is, when an operation for entering P and Q is performed by employing the operating unit 34, the system controller 36 outputs these values to the noise reduction unit 28. The noise reduction unit 28 performs the process in step S102 based on the values of P and Q output by the system controller 36. In a case wherein P and Q are odd numbers, the location of the target pixel can be employed as the median point to set a computation window.

Figure 4:
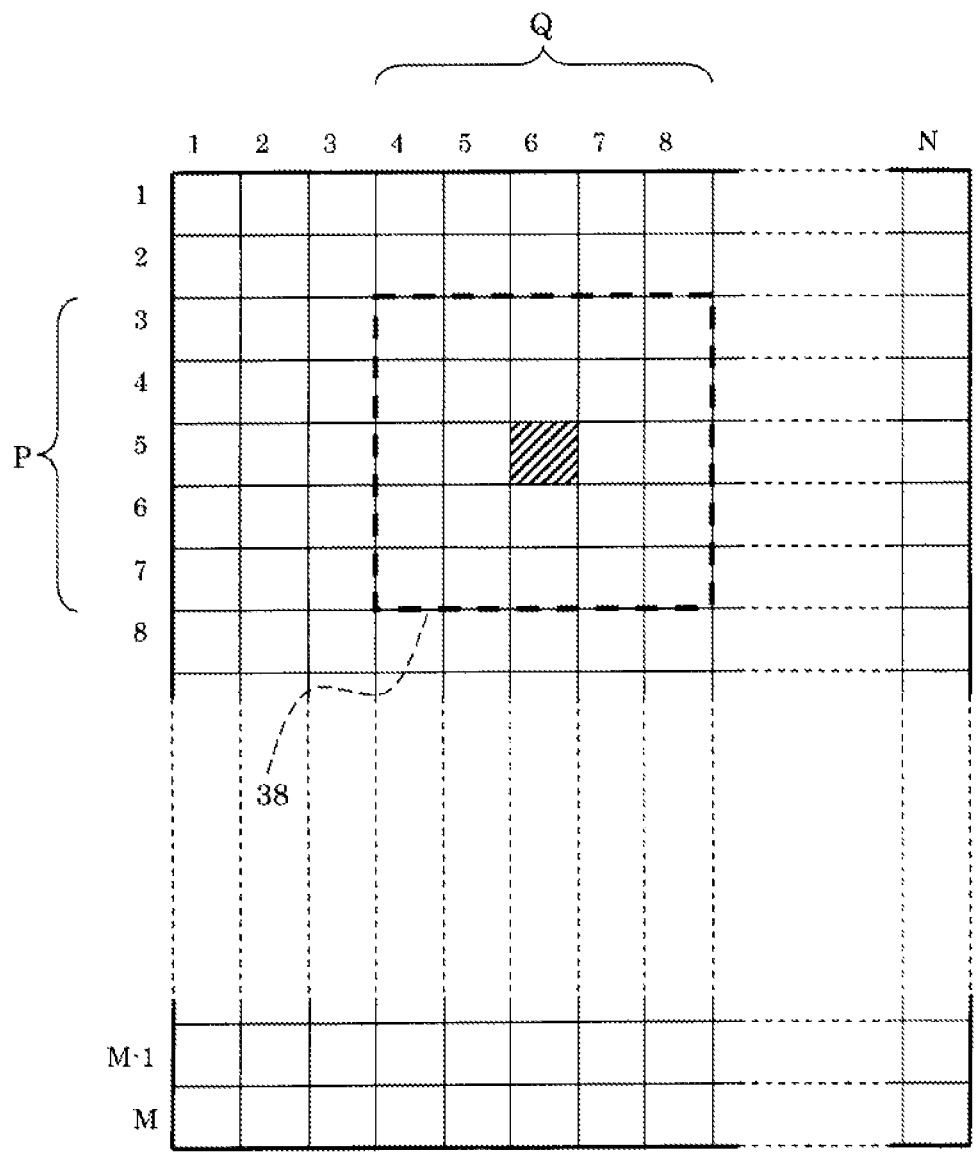
FIG. 4 A diagram for explaining the processing for setting a computation window.

In an example shown in FIG. 4, a target pixel is indicated by a hatched area, and a computation window 38 is indicated by a dashed line. In this example, line data at time address of 6 are employed for the noise reduction process, and a pixel at a velocity address of 5 is designated as a target pixel. Further, the computation window 38 with P=Q=5 is set by employing the target pixel as the median point.

The noise reduction unit 28 calculates the mean value a and dispersion d of the pixel values of pixels included in the computation window (S103). The mean value a serves as a significant value that indicates a tendency of the magnitudes of pixel values for the computation window. For this technical sense, a statistical value other than the mean value a may be employed. The dispersion is a significant statistical value that indicates a distribution of pixel values, such as a variance or a standard deviation, and that represents the tendency of dispersion of the pixel values for the computation window. The variance is defined as $(1/n)\Sigma(Xi-a)^2$. Here, n denotes the number of pixels included in the computation window. Xi denotes the pixel value of a pixel included in the computation window, and i denotes an integer (1 to n) to specify a pixel. Σ indicates summation of i=1 to n. Further, a standard deviation is defined as the square root of a variance. As another definition of dispersion, $(1/n)\Sigma|Xi-a|$ may be employed.

Figure 5:
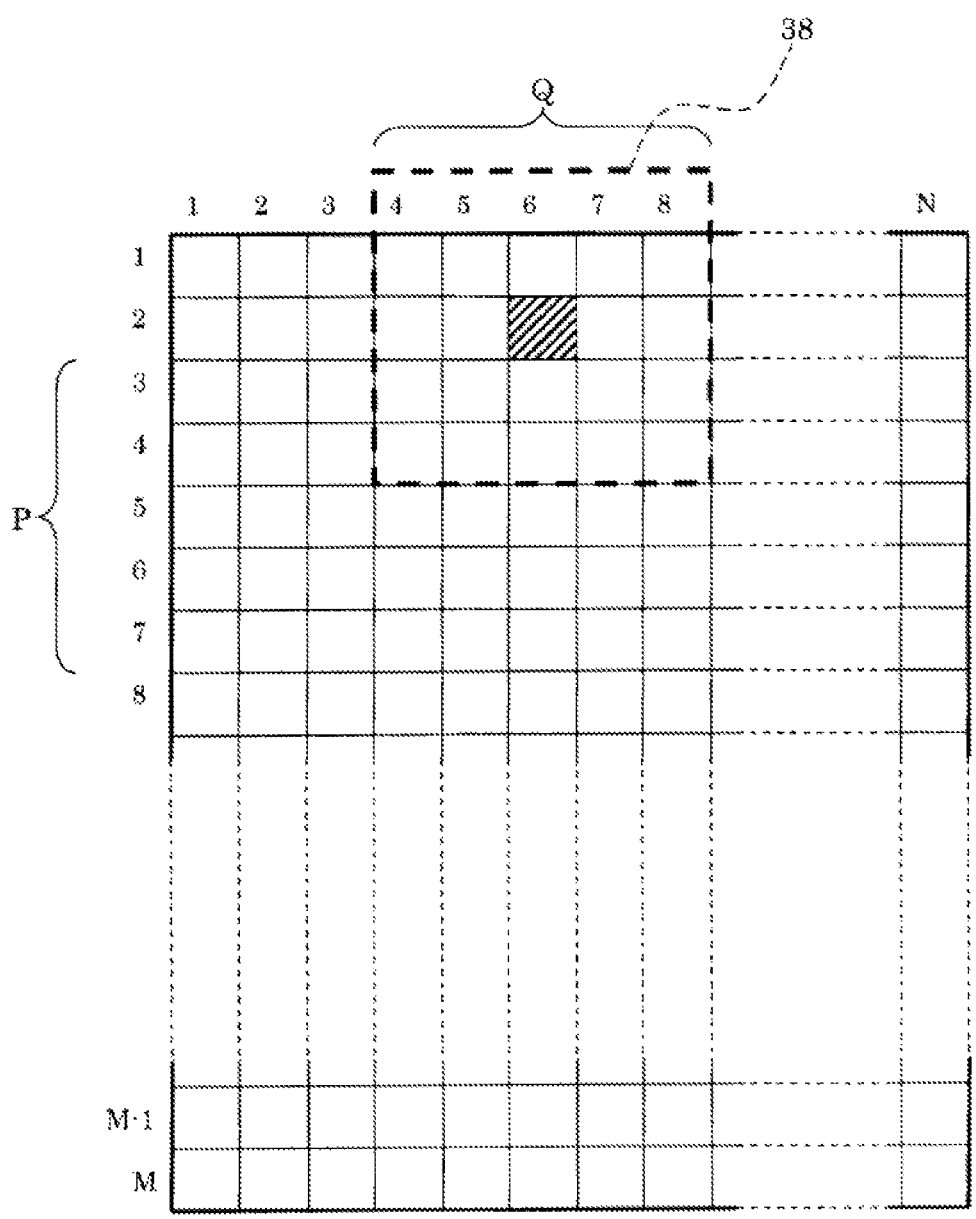
FIG. 5 A conceptual diagram showing the state wherein the computation window is extended across a pixel arrangement area.

In a case wherein a constant positional relationship is established for the computation window and the target pixel, the computation window may be extended outside a pixel arrangement area, depending on the location of the target pixel. For example, in a case wherein the target pixel is located at the median point of the computation window with P=Q=5, the computation window is extended outside the pixel arrangement area when the velocity address of the target pixel is 1, 2, M−1, or M. The conceptual state in FIG. 5 indicates that the topmost row in the computation window 38 is outside the pixel arrangement area. In this case, the area of the computation window extended outside the pixel arrangement area is not taken into account for calculation of the mean value a and the dispersion d of the pixel values. That is, according to the example in FIG. 5, the topmost row in the computation window 38 is not employed for calculation of the mean value a and the dispersion d of the pixel values, and the second to the fifth rows in the computation window are regarded as a population to calculate the mean value a and the dispersion d of the pixel values with n=20.

When the mean value a and the dispersion d have been obtained, the noise reduction unit 28 determines whether the mean value a is equal to or smaller than a threshold value T1 for evaluation of the mean value (S104). The threshold value T1 is a value that tends to be increased when the pixel value of a noise pixel in a Doppler waveform image is increased, and is obtained, as will be described later, by statistical calculation based on the pixel values in a predetermined sample area designated in the pixel arrangement area.

When the mean value a is greater than the threshold value T1, the noise reduction unit 28 determines that the target pixel is not a noise pixel, and maintains the pixel value of the target pixel (S105). When the mean value a is equal to or smaller than the threshold value T1, the noise reduction unit 28 determines whether the dispersion d is equal to or smaller than a threshold value T2 for evaluation of dispersion (S106). The threshold value T2 is a value obtained based on the operation by a user. That is, when the operation for entering the threshold value T2 is performed by using the operating unit 34, the system controller 36 outputs the threshold value T2 to the noise reduction unit 28. The noise reduction unit 28 employs the threshold value T2 output by the system controller 36, and performs the process at step S106.

When the dispersion d is greater than the threshold value T2, the noise reduction unit 28 determines that the target pixel is not a noise pixel, and maintains the pixel value of the target pixel (S105). When the dispersion d is equal to or smaller than the threshold value T2, the noise reduction unit 28 ascertains that the target pixel is a noise pixel, and employs, as a new pixel value for the target pixel, a value obtained by multiplying the pixel value of the target pixel by the weighting factor w (S107). Here, as with the threshold value T2, the weighting factor w is a value obtained based on the operation of the user. The noise reduction unit 28 determines whether all of the pixels indicated by the line data to be processed are designated as target pixels (S108). In a case wherein there is still a pixel that is not yet designated as a target pixel, program control returns to step S101, and a new pixel is additionally designated as a target pixel. In a case wherein all of the pixels of the line data to be processed have been designated as target pixels, the line data for which the process has been completed are output to the image generator 30 (S109).

According to the processing performed in steps S101 to S107, the computation window is set for one pixel that belongs to a pixel group indicated by the line data to be processed, and that is designated as a target pixel. Thereafter, the mean value a and the dispersion d are calculated for the pixel values for the computation window. Further, when the mean value a is equal to or smaller than the threshold value T1, and when the dispersion d is equal to or smaller than the threshold value T2, it is ascertained that the target pixel is a noise pixel, and the pixel value of the target pixel is reduced.

The noise reduction unit 28 designates, in order, as a target pixel, the individual pixels indicated by the line data to be processed, and performs the processes in steps S101 to S108. When the noise reduction process has been performed for all of the pixels indicated by the line data to be processed, the line data that have been processed are output to the image generator 30 (S109).

Each time updating is performed for the line data, for which the noise reduction process is to be performed, the noise reduction unit 28 performs the noise reduction process for the pertinent line data, and outputs to the image generator 30 the line data obtained via the noise reduction process. The image generator 30 generates Doppler waveform image data based on the line data sequentially output by the noise reduction unit 28, and displays a Doppler waveform image on the display device 32.

An explanation will be given for the theory by which determination can be performed as to whether the target pixel is a noise pixel. Generally, pixels in an area designated in a Doppler waveform image are categorized as follows in accordance with the mean value and dispersion in the area: (i) both the mean value and dispersion are small; (ii) the mean value is large, while the dispersion is small; (iii) the mean value is small, while the dispersion is large; and (iv) both the mean value and the dispersion are large.

There is a tendency that the pixel value of a noise pixel is smaller than the pixel that represents the shape of the Doppler waveform, and dispersion for the pixel value of the noise pixel is small. Therefore, a pixel categorized into (i) can be regarded as a noise pixel. Further, the pixel value of a pixel that represents the shape of the Doppler waveform is larger than the pixel value of the noise pixel, and dispersion for the pixel value is small. Therefore, there is a high possibility that the pixel categorized into (ii) is a pixel that represents the shape of the Doppler waveform. Further, there is a high possibility that the pixels categorized into (iii) and (iv) are those representing the boundary area between the shape of the Doppler wave and the noise in the background.

The noise reduction process according to the present invention is a process in which this theory is employed to determine whether the target pixel is a noise pixel. That is, it is assumed that a target pixel, for which the mean value a in a corresponding computation window is the threshold value T1 or smaller, and dispersion for the corresponding computation window is the threshold value T2 or smaller, is a noise pixel, while both the mean value and the dispersion for the computation window are regarded as small. The pixel value for the target pixel that is regarded as a noise pixel is reduced.

In a case wherein the mean value a for the corresponding computation window is equal to or smaller than the threshold value T1, the target pixel is categorized into (i) or (iii). In a case wherein the frequency at which categorizing of a pixel into (i) occurs is higher than the frequency at which categorizing of a pixel into (iii) occurs, only a condition wherein the mean value a for the corresponding computation window is the threshold value T1 or smaller may be employed to determine that the target pixel is a noise pixel. In this case, the process in step S106 may be skipped and not performed.

Furthermore, in a case wherein the dispersion d for the corresponding computation window is the threshold value T2 or smaller, the target pixel is categorized into (i) or (ii). In a case wherein the frequency at which categorizing of a pixel into (i) occurs is higher than the frequency at which categorizing of a pixel into (ii) occurs, only a condition wherein the dispersion d for the corresponding computation window is the threshold value T2 or smaller may be employed to determined that the target pixel is a noise pixel. In this case, the process at step S104 may be skipped, and not performed.

In this embodiment, the mean value is employed as a value indicating the tendency of the magnitude of a pixel value for the computation window. A value indicating the tendency of the magnitude of the pixel value for the computation window is not limited to the mean value. For example, there can be employed a statistical value, such as the median or a central value, or a value obtained by adding a constant value to the mean value.

Further, in step S107, instead of employing, as a new pixel value for the target value, a value obtained by multiplying the pixel value of the target pixel by the weighting factor w, a process for subtracting a predetermined value from the pixel value of the target pixel may be performed.

(3) Process for Determining Threshold Value T1 for Evaluation of Mean Value

The process for determining the threshold value T1 used in step S104 will be described. Before the processing in the flowchart in FIG. 3 is started, the threshold value T1 is obtained by statistical calculation based on the pixel values in a sample area designated in the pixel arrangement area.

Figure 6:
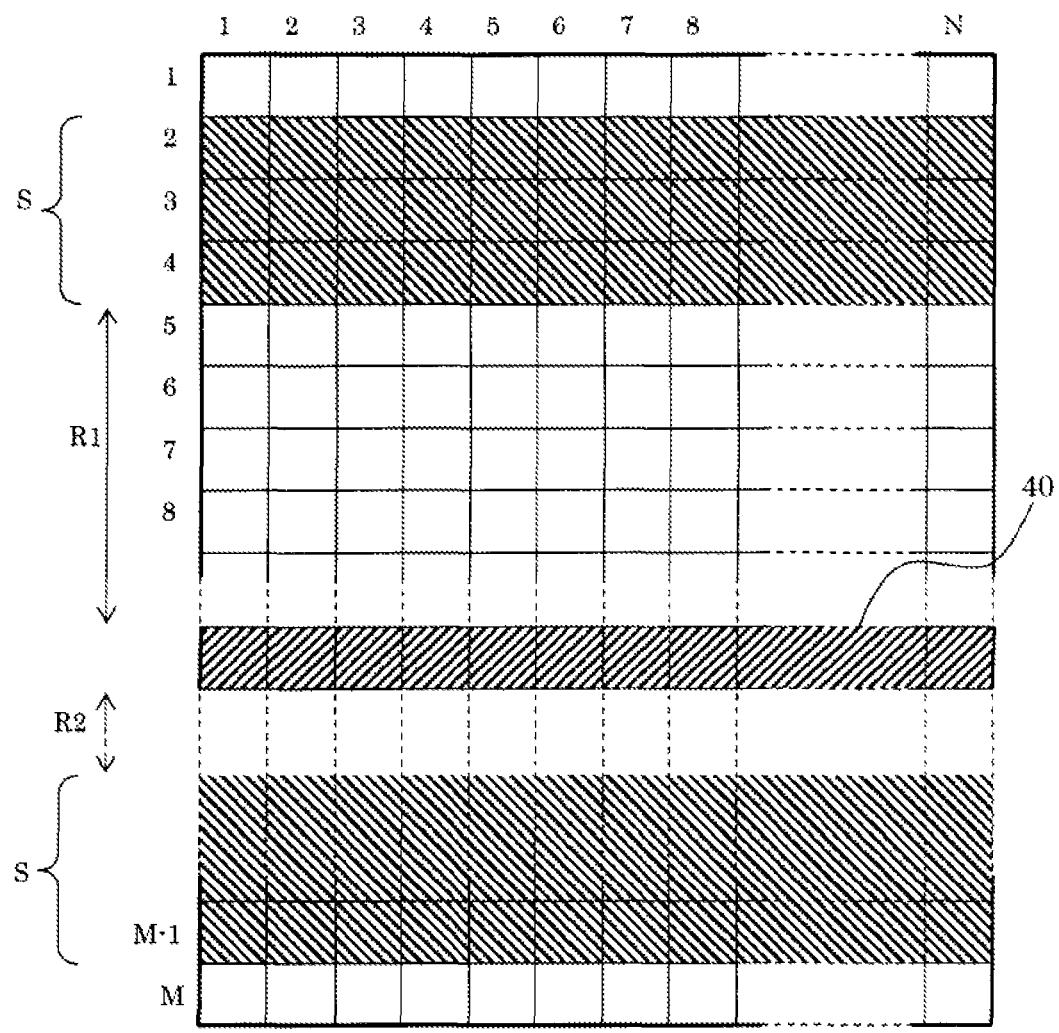
FIG. 6 A diagram for explaining the processing for designating a sample area.

The noise reduction unit 28 designates a sample area in the pixel arrangement area. The sample area is designated to an area where many noise pixels tends to be present, while the base line in a Doppler waveform image indicating the velocity of zero is employed as a reference. As shown in FIG. 6, for example, the sample areas are defined as areas consisting of a predetermined number of rows S, one that is located apart from a row 40 that represents a base line, at a distance of a predetermined pixel count R1 in the positive direction along the velocity axis (in the upward direction), and the other that is located apart at a distance of a predetermined pixel count R2 in the negative direction along the velocity axis (in the downward direction). Through the process performed by the high-pass filters 20I and 20Q, the pixel values of the individual pixels that form the row corresponding to the base line are the local minimum values. Therefore, in the pixel arrangement area, the noise reduction unit 28 designates, as the row 40 representing the base line, the line of pixels that have the local minimum values, and sets, as sample areas, areas consisting of the predetermined number of rows S, one located apart from the row 40 representing the base line at a distance of the predetermined pixel count R1 in the positive direction along the velocity axis, and the other located at a distance of the predetermined pixel count R2 in the negative direction along the velocity axis.

Instead of setting the sample areas in this manner, an area having the continuous addresses 1 to S and an area having the continuous addresses M−S+1 to M; i.e., upper and lower areas consisting of S rows in the pixel arrangement area, may also be set as sample areas. Furthermore, the number of rows may differ between the upper and lower sample areas.

In the processing for determining the threshold value T1, the noise reduction unit 28 performs the following process for the individual line data sets. Specifically, among a pixel group for one column indicated by one line data set, the maximum value of the pixel values for the portion employed as a sample area is obtained as a noise sample value. According to the example in FIG. 6, since two sample areas are provided, one noise sample value is obtained for the pixels that are included in a pixel group for one column and that belong to the two portions employed as the sample areas. The noise reduction unit 28 employs the noise sample values obtained for the individual line data sets, and obtains, as the threshold value T1, the mean value of the noise sample values for all of the line data.

Instead of employing all of the line data sets, predesignated line data sets may be employed among all of those to calculate the noise sample values, and the mean value for the noise sample values for the predesignated line data sets may be regarded as the threshold value T1. Furthermore, instead of obtaining the maximum value of the pixel values in the sample area as the noise sample value, another statistical value, such as the mean value, the central value, or the median, for the pixel values in the sample area may also be calculated as the noise sample value.

According to this processing, the area consisting of a predetermined number of rows, located at a distance of a predetermined pixel count from the row indicating the base line, is designated as a sample area, and the statistical process is performed for the pixels included in the sample area to calculate the threshold value T1. Generally, in the Doppler waveform image, many noise pixels tend to be present in an area apart from the base line at a predetermined distance or longer. Therefore, in the sample areas designated as shown in FIG. 6, there is a tendency that many noise pixels are present. Therefore, when the pixel values of the noise pixels in the Doppler waveform image tend to be increased, the threshold value T1 becomes large.

(4) Effects Provided Through Noise Reduction Process

Through the noise reduction process according to the present invention, as will be explained below, a Doppler waveform image can be generated by appropriately increasing the visibility of the image in accordance with a change of the measurement condition. Specifically, the area for the computation window designated in the noise reduction process extends the pixels of the individual sets of line data that were stored in the buffer memory 26 earlier or later than the line data to be processed. Therefore, the mean value a of the pixel values for the computation window is adaptively set by taking into account the sets of line data that were generated earlier or later than the line data to be processed. Furthermore, when the pixel value of the noise pixel in the Doppler waveform image tends to be increased, there is an increase in the threshold value T1 that is to be compared with the mean value a to determine whether the target pixel is a noise pixel. As a result, in a case wherein the pixel value of the noise pixel is changed by, for example, altering the measurement condition during the diagnostic performance, the visibility of the Doppler waveform image can be adaptively improved.

(5) Designation of Velocity Range for Measurement

Designation of a velocity range for measurement will now be described while referring to FIG. 1. For the ultrasound diagnostic apparatus according to this embodiment, the velocity range for measurement is designated based on the operation by a user. Further, the designated velocity range is employed to determine, for example, a sampling frequency fs employed by the A/D converters 18I and 18Q and a velocity display range on the display device 32.

When the velocity range of equal to or higher than −Vm to equal to or lower than Vm is designated by manipulating the operating unit 34, the system controller 36 obtains a sampling frequency as $fs = \alpha \cdot 4 Vm/\lambda$. Here, $\lambda$ is a wavelength for an ultrasonic wave propagating to and from a subject, and $\alpha$ is a value obtained by multiplying 2 by a natural number; i.e., 2, 4, 8, 16, . . . . The system controller 36 outputs the obtained sampling frequency fs to the A/D converters 18I and 18Q. The A/D converters 18I and 18Q perform the sampling process based on the sampling frequency output by the system controller 36.

Figure 7:
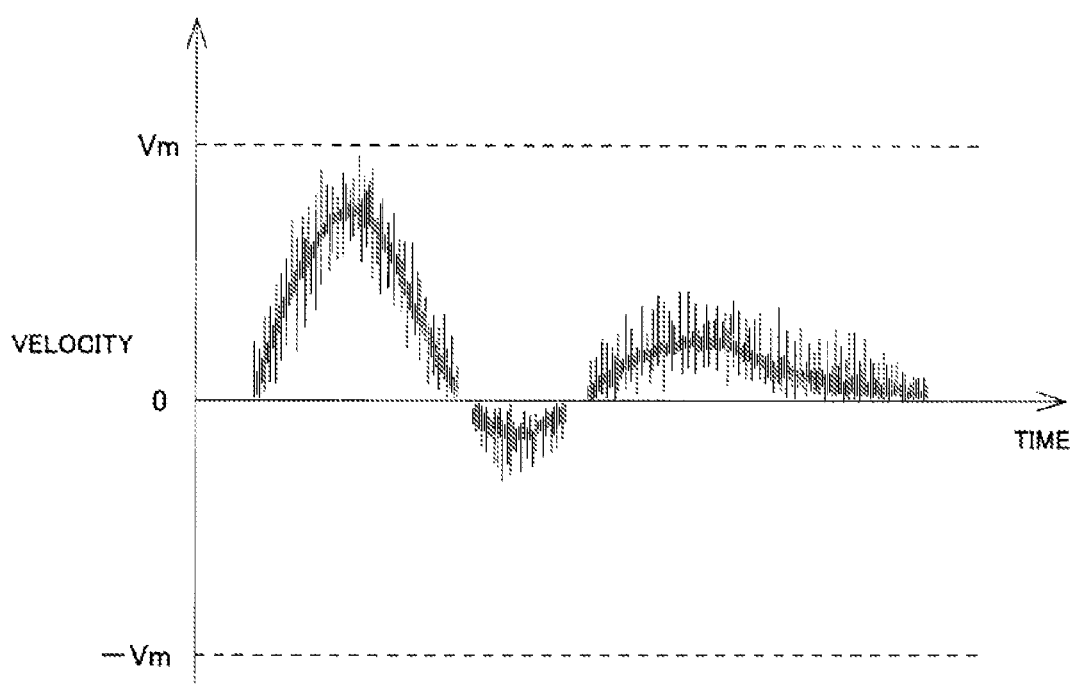
FIG. 7 A diagram showing an example image displayed on a display device.

Under the control performed by the system controller 36, the image generator 30 generates a Doppler waveform image in the velocity range of −Vm or higher to Vm or lower. Example images displayed on the display device 32 in this case are shown in FIG. 7 and FIG. 8A.

Figure 8A:
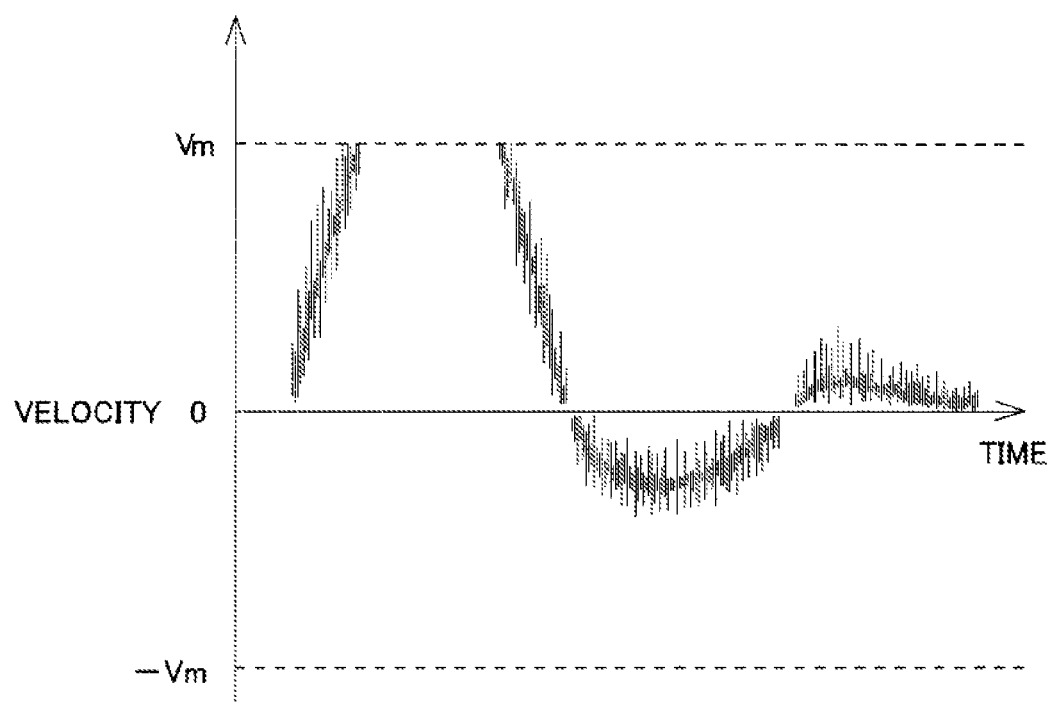
FIG. 8A A diagram showing an example image displayed on the display device.
Figure 8B:
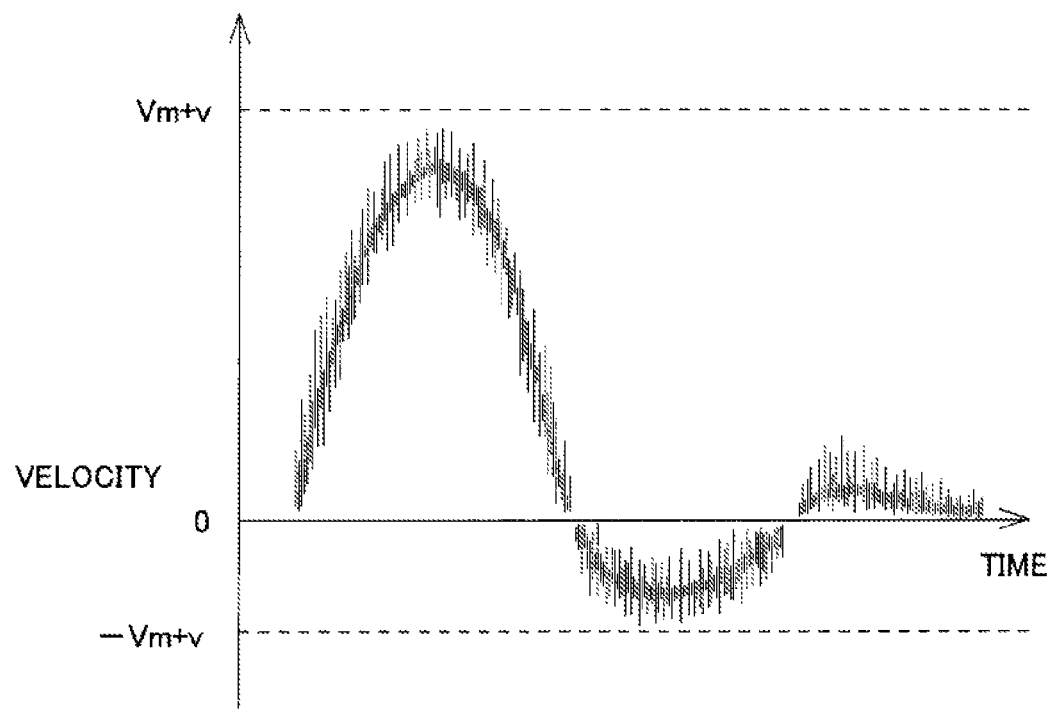
FIG. 8B A diagram showing an example image displayed on the display device.

In a case wherein, as shown in FIG. 8A, the measured velocity exceeds the upper limit of Vm, the operation for moving the base line is performed, and the entire waveform can be displayed as in the example in FIG. 8B. According to the example in FIG. 8B, the display range is set equal to or higher than −Vm+v to equal to or lower than Vm+v.

Figure 9:
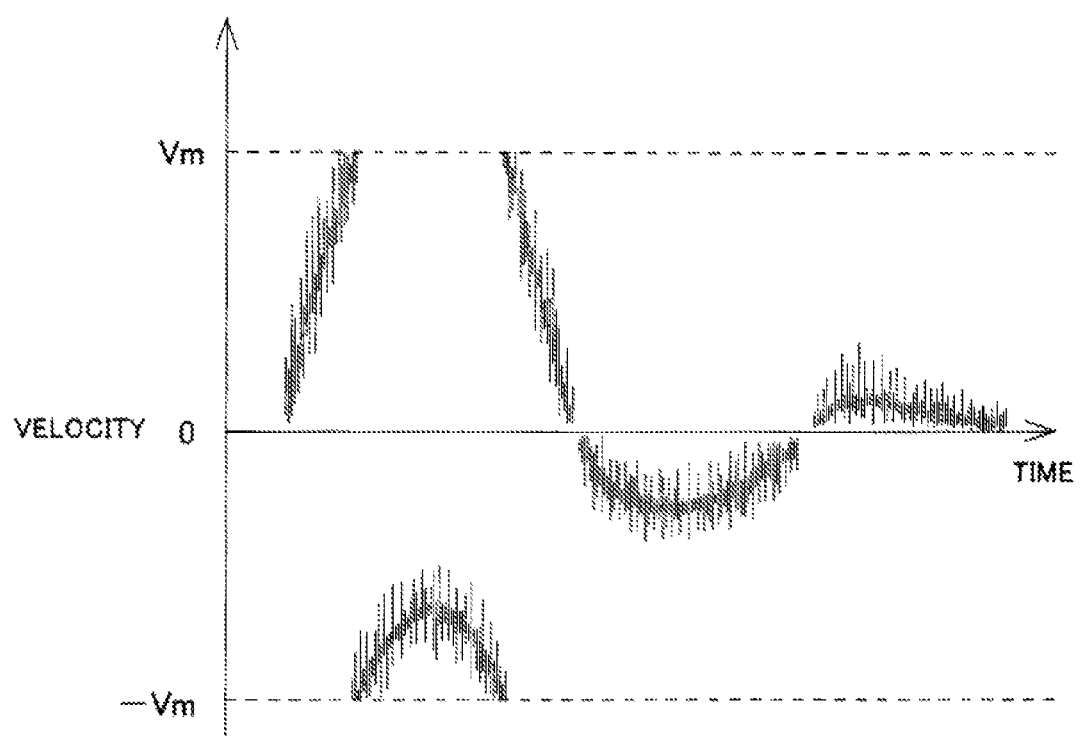
FIG. 9 A diagram showing the occurrence of a folding phenomenon due to aliasing.
Figure 10:
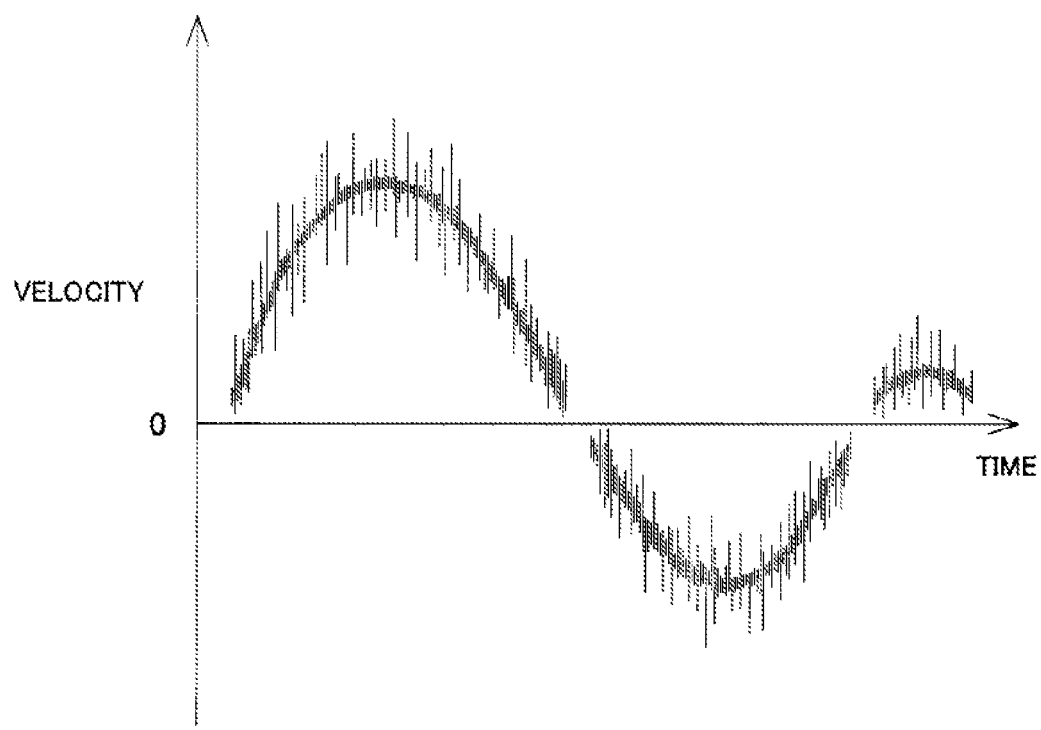
FIG. 10 A diagram showing a Doppler waveform image.

For the conventional ultrasound diagnostic apparatus, when the velocity range of −Vm or higher to Vm or lower is designated, the sampling frequency fs is generally set as fs=4 Vm/λ according to the sampling theorem. Here, fs=4 Vm/λ corresponds to the bandwidth that corresponds to the measurement velocity range, and is extended between the positive and negative Doppler shift frequencies. Therefore, the velocity range to be displayed is a range where the Doppler shift frequency is equal to or smaller than fs/2; i.e., a range of −Vm or higher to Vm or lower, and when the velocity of a subject to be measured, such as blood, exceeds the range, a folding phenomenon might occur due to aliasing, as shown in FIG. 9. This folding phenomenon is a phenomenon that a waveform with a velocity of Vm or higher is displayed by being shifted at a distance of 2 Vm in the negative direction.

For the ultrasound diagnostic apparatus according to this embodiment, the sampling frequency is designated as fs=α·4 Vm/λ, as described above. Here, fs=α·4 Vm/λ is a frequency higher than the bandwidth that corresponds to the measurement velocity range and is extended between the positive and negative Doppler shift frequencies. Therefore, the velocity range to be displayed is a range where the Doppler shift frequency is fs/2 or lower; i.e., a range of −α·Vm or higher to α·Vm or lower. Therefore, according to the example in FIG. 8B, when Vm+v is equal to or lower than α·Vm, the Doppler waveform image can be displayed without causing the folding phenomenon. Furthermore, since the sampling frequency is set higher than the conventional frequency, noise outside the velocity measurement range that is to be superimposed on the velocity measurement range can be reduced, and the S/N ratio of the Doppler waveform image can be improved.

REFERENCE SIGNS LIST

10: transmission signal generator
12: transmission oscillator
14: reception oscillator
16: quadrature detector
18I, 18Q: A/D converter
20I, 20Q: high-pass filter
22: FFT calculator
24: line data generator
26: buffer memory
28: noise reduction unit
30: image generator
32: display device
34: operating unit
36: system controller
38: computation window
40: row representing a base line

The invention claimed is:

1. An ultrasound image processing apparatus, comprising:
a frequency-analyzing unit, for generating frequency spectrum data on Doppler shift frequency components of ultrasonic waves that have been transmitted toward a subject and reflected from the subject, and are thereafter received;
a line data generating unit, for employing the frequency spectrum data to generate line data for an arrangement of a plurality of pixels, each pixel having a pixel value determined in accordance with a corresponding frequency, and individual pixel values represent magnitudes of the Doppler shift frequency components;
a window designating unit for designating a computation window region in a Doppler waveform image that would be formed using a matrix of a plurality of the line data generated in time series, the window region shifting through different subsets of the matrix for different target pixels;
a trend value calculating unit for calculating, for each window region, a trend value that indicates a tendency for magnitudes of the pixel values in the window region;
a threshold value determining unit for determining a threshold value for evaluation of the trend value using the plurality of pixel values in a predetermined area of the Doppler waveform image that would be formed;
a dispersion calculating unit for obtaining, for each window region, a dispersion of pixel values using the pixel values of the pixels included in each window region;
a pixel value adjusting unit for reducing the pixel value of the target pixel in each window region when the trend value is smaller than or equal to the evaluation threshold value and the dispersion of pixel values is smaller than or equal to a predetermined second evaluation threshold value; and
an image generator generating a Doppler waveform image using the matrix of the plurality of line data generated in time series after processing by the pixel value adjusting unit.

2. The ultrasound image processing apparatus according to claim 1, wherein
the predetermined area of the Doppler waveform image that would be formed is an area located apart from the base line indicating a velocity of zero, in a direction along the line data, at a distance equivalent to a predetermined number of pixels, and
for each of the plurality of the line data that would form the Doppler waveform image, the threshold value determining unit calculates statistical values with respect to the plurality of pixel values in an area that is one part of the predetermined area, and calculates the evaluation threshold value based on the statistical values obtained for each of the plurality of the line data.

3. The ultrasound image processing apparatus according to claim 1, wherein the frequency-analyzing unit includes:
a measurement range acquiring unit for obtaining a velocity measurement range in accordance with an operation by a user;
a sampling unit for performing sampling for a signal received based on the received ultrasonic wave by employing a sampling frequency higher than a bandwidth that corresponds to the velocity measurement range and that is extended between positive and negative Doppler shift frequencies; and a converting unit for generating the frequency spectrum data based on a Fourier transform for the received signal obtained by sampling.

4. The ultrasound image processing apparatus according to claim 1, wherein the pixel value adjusting unit maintains the pixel value of the target pixel in each window region when the trend value exceeds the evaluation threshold value, or when the dispersion exceeds the second evaluation threshold value.

5. An ultrasound image processing method causing a processor to perform:

- a frequency-analyzing process generating frequency spectrum data on Doppler shift frequency components of ultrasonic waves that have been transmitted toward a subject and reflected from the subject, and are thereafter received;
- a line data generating process employing the frequency spectrum data to generate line data for an arrangement of a plurality of pixels, each pixel having a pixel value determined in accordance with a corresponding frequency, and individual pixel values represent magnitudes of the Doppler shift frequency components;
- a window designating process designating a computation window region in a Doppler waveform image that would be formed using a matrix of a plurality of the line data generated in time series, the window region shifting through different subsets of the matrix for different target pixels;
- a trend value calculating process, for calculating, for each window region, a trend value that indicates a tendency for magnitudes of pixel values in the window region;
- a threshold value determining process determining a threshold value for evaluation of the trend value using the plurality of pixel values in a predetermined area of the Doppler waveform image that would be formed;
- a dispersion calculating process obtaining, for each window region, a dispersion of pixel values using the pixel values of the pixels included in the window region;
- a pixel value adjusting process, for adjusting the pixel value of the target pixel in each window region based on a result obtained by comparing the trend value with the evaluation threshold value and by comparing the dispersion of pixel values with a predetermined second evaluation threshold value; and
- generating a Doppler waveform image using the matrix of the plurality of line data generated in time series after the pixel value adjusting process.

* * * * *